(12) United States Patent
Iwaki et al.

(10) Patent No.: US 12,213,966 B2
(45) Date of Patent: Feb. 4, 2025

(54) METHODS OF REDUCING PLASMA LEVEL OF MACROPHAGE MIGRATORY INHIBITORY FACTOR IN PATIENTS

(71) Applicant: MediciNova, Inc., La Jolla, CA (US)

(72) Inventors: Yuichi Iwaki, La Jolla, CA (US); Kazuko Matsuda, La Jolla, CA (US)

(73) Assignee: MediciNova, Inc., La Jolla, CA (US)

( * ) Notice: Subject to any disclaimer, the term of this patent is extended or adjusted under 35 U.S.C. 154(b) by 187 days.

(21) Appl. No.: 17/222,673

(22) Filed: Apr. 5, 2021

(65) Prior Publication Data

US 2021/0308109 A1 Oct. 7, 2021

Related U.S. Application Data

(60) Provisional application No. 63/005,792, filed on Apr. 6, 2020.

(51) Int. Cl.
*A61K 31/437* (2006.01)
*A61K 9/00* (2006.01)
*A61K 9/48* (2006.01)
*A61P 11/00* (2006.01)

(52) U.S. Cl.
CPC .......... *A61K 31/437* (2013.01); *A61K 9/0053* (2013.01); *A61K 9/48* (2013.01); *A61P 11/00* (2018.01)

(58) Field of Classification Search
CPC ...... A61K 31/437; A61K 9/48; A61K 9/0053; A61P 11/00
See application file for complete search history.

(56) References Cited

U.S. PATENT DOCUMENTS

| | | | |
|---|---|---|---|
| 6,395,747 B1 | 5/2002 | Sakoda et al. | |
| 8,138,201 B2 | 3/2012 | Kalafer et al. | |
| 9,314,452 B2 | 4/2016 | Kalafer et al. | |
| 2006/0160843 A1 | 7/2006 | Johnson et al. | |
| 2009/0221629 A1* | 9/2009 | Johnson | A61P 25/32 514/300 |

FOREIGN PATENT DOCUMENTS

| | | |
|---|---|---|
| WO | WO2005/051293 A2 | 6/2005 |
| WO | WO 2009/009529 A1 | 1/2009 |
| WO | WO 2019/157428 A1 | 8/2019 |

OTHER PUBLICATIONS

Luyt, "Virus-induced acute respiratory distress syndrome: Epidemiology, management and outcome", Presse Med., Dec. 2011; 40(12): e561-e568.*
International Preliminary Report on Patentability issued in International Patent Application No. PCT/US2021/025732, dated Oct. 20, 2022.
Clanchy et al., "Ibudilast Inhibits Chemokine Expression in Rheumatoid Arthritis Synovial Fibroblasts and Exhibits Immunomodulatory Activity in Experimental Arthritis", *Arthritis & Rheumatology*, vol. 71, No. 5, Apr. 12, 2019, pp. 703-711.
Dheir et al., "Does Macrophage Migration Inhibitory factor Predict the Prognosis of Covid-19 Disease?", *The Journal of Infection in Developing Countries*, vol. 15, No. 03, Mar. 31, 2021, pp. 398-403.
Foreign Search Report on PCT PCT/US2021/025732 DTD Jul. 2, 2021.
Lai et al., "Role For Macrophage Migration Inhibitory Factor in Acute Respiratory Distress Syndrome", *The Journal of Pathology*, vol. 199, No. 4, Apr. 1, 2003, pp. 496-508.
Rolan et al., "Ibudilast: A Review of Its Pharmacology, Efficacy and Safety in Respiratory and Neurological Disease", *Expert Opin Pharmocother.*, Ashley Publications Ltd, London, UK, vol. 10, No. 17, Dec. 1, 2009, pp. 2897-2904.
Thierry et al., "Macrophage Migration Inhibitory Factor: a Regulator of Innate Immunity", *Nature Reviews Immunology*, vol. 3, No. 10, Oct. 1, 2003, pp. 791-800.
Yang et a., "Ibudilast, a Phosphodiesterase-4 Inhibitor, Ameliorates Acute Respiratory Distress Syndrome in Neonatal Mice by Alleviating Inflammation and Apoptosis", *Medical Science Monitor*, vol. 26, No. 26, Feb. 7, 2020, 8 pages.
Cho, et al., "Allosteric Inhibition of Macrophage Migration Inhibitory Factor Revealed by Ibudilast," PNAS, vol. 107, No. 25, pp. 11313-11318 (2010).
Gibson et al., "The Inhibitory Profile of Ibudilast Against the Human Phosphodiesterase Enzyme Family," European Journal of Pharmacology, vol. 538, pp. 39-42 (2006).
Sanftner et al., "Cross-species comparisons of the pharmacokinetics of ibudilast," Xenobiotica, vol. 39, No. 12, pp. 964-977 (Nov. 2009). [Abstract].
Obernolte, R., et al. (1993) "The cDNA of a human lymphocyte cyclic-AMP phosphodiesterase (PDE IV) reveals a multigene family" Gene 129: 239-247.
Rile et al., "Potentiation of Ibudilast Inhibition of Platelet Aggregation in the Presence of Endothelial Cells," Thrombosis Research, 102 239-246 (2001).
Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).
Suzumura et al., "Ibudilast suppresses TNF.alpha. production by glial cells functioning mainly as type III phosphodiesterase inhibitor in NCS," Brain Research, 837:203-212 (1999).
Takuma et al., "Ibudilast attenuates actrocyte apoptsis via cyclic GMP signaling pathway in an in vitro reperfusion model," British Journal of Pharmacology, 133:841-848 (2001).
Jeffery et al., "The preparation and characterization of poly(lactide-co-glycolide) microparticles. II. The Entrapment of a Model Protein Using a (water-in-oil)-in-water Emulsion Solvent Evaporation Technique," Pharm. Research, vol. 10, pp. 362-368 (1993).

(Continued)

*Primary Examiner* — Noble E Jarrell
*Assistant Examiner* — Richard Grant Peckham
(74) *Attorney, Agent, or Firm* — Foley & Lardner LLP

(57) ABSTRACT

Disclosed is a method of reducing plasma level of macrophage migratory inhibitory factor in a subject in need thereof, the method comprising administering to the subject a therapeutically effective amount of ibudilast, or a pharmaceutical salt thereof.

11 Claims, No Drawings

(56) References Cited

OTHER PUBLICATIONS

Yang, et al., "The Emerging Role of Toll-Like Receptor 4 in Myocardial Inflammation," *Cell Death and Disease*, vol. 7, e2234, 10 pages (2016).

Hou, "Role of macrophage migration inhibitory factor in influenza H5N1 virus pneumonia", Acta Viral, vol. 53, No. 4, Jan. 1, 2009, pp. 225-231.

Official Communication issued in co-pending European Patent Application No. 21721728.0, dated Oct. 23, 2024.

Souza, et al., "Macrophage migration inhibitory factor (MIF) controls cytokine release during respiratory syncytial virus infection in macrophages", Inflammation Research, vol. 68, No. 6 pp. 481-491 (2019).

* cited by examiner

METHODS OF REDUCING PLASMA LEVEL OF MACROPHAGE MIGRATORY INHIBITORY FACTOR IN PATIENTS

CROSS REFERENCE TO RELATED APPLICATIONS

This application claims the benefit of U.S. Provisional Patent Application No. 63/005,792, filed Apr. 6, 2020, which is incorporated by reference herein in its entirety.

BACKGROUND

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News.Medical-.Net; Pharmaceutical News, 2 Aug. 2005). As disclosed in this publication, this clinical trial was expected to treat "relapsing-remitting MS," however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. U.S. Patent Application Publication No. 20060160843 discloses ibudilast for the treatment of intermittent and short term pain, however, this is not pain related to a progressive neurodegenerative disease. However, U.S. Pat. No. 9,314,452 discloses ibudilast as a treatment for amyotrophic lateral sclerosis, a progressive neurodegenerative disease. Similarly, U.S. Pat. No. 8,138,201 discloses ibudilast as a treatment for primary progressive multiple sclerosis and/or secondary progressive multiple sclerosis.

While the use of ibudilast for a number of varying indications has been reported to date, to the best of the inventors' knowledge, its use in reducing plasma level of macrophage migratory inhibitory factor (MIF) in patients has heretofore remained largely unexplored.

SUMMARY

In one aspect, disclosed herein is a method of reducing plasma level of macrophage migratory inhibitory factor (MIF) in a subject in need thereof, the method comprising administering to the subject a therapeutically effective amount of ibudilast, or a pharmaceutical salt thereof.

In some embodiments, ibudilast, or the pharmaceutically acceptable salt thereof, is administered orally. In some embodiments, ibudilast, or the pharmaceutically acceptable salt thereof, is administered intravenously. In some embodiments, ibudilast, or the pharmaceutically acceptable salt thereof, is administered by subcutaneous injection. In some embodiments, ibudilast, or the pharmaceutically acceptable salt thereof, is administered by intramuscular injection. In some embodiments, ibudilast, or the pharmaceutically acceptable salt thereof, is administered by inhalation.

In some embodiments, ibudilast, or the pharmaceutically acceptable salt thereof, is administered for 1, 2, 3, 4, 5, 6, 7, 8, 9, or 10 days, or more. In some embodiments, ibudilast, or the pharmaceutically acceptable salt thereof, is administered for at least 3 months. In some embodiments, ibudilast, or the pharmaceutically acceptable salt thereof, is administered for at least one year. In some embodiments, ibudilast, or the pharmaceutically acceptable salt thereof, is administered for at least two years.

In some embodiments, ibudilast, or the pharmaceutically acceptable salt thereof, is administered at least once daily. In some embodiments, ibudilast, or the pharmaceutically acceptable salt thereof, is administered twice daily.

In some embodiments, the therapeutically effective amount of ibudilast, or the pharmaceutically acceptable salt thereof, is from 0.1 mg to 720 mg per day. In some embodiments, the therapeutically effective amount of ibudilast, or the pharmaceutically acceptable salt thereof, is from 30 mg to 200 mg per day. In some embodiments, the therapeutically effective amount of ibudilast, or the pharmaceutically acceptable salt thereof, is 40 mg to 600 mg daily. In some embodiments, the therapeutically effective amount of ibudilast, or the pharmaceutically acceptable salt thereof, is 100 mg to 480 mg daily. In some embodiments, the therapeutically effective amount of ibudilast, or the pharmaceutically acceptable salt thereof, is selected from the group consisting of 30 mg/day, 60 mg/day, 90 mg/day, 100 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

In some embodiments, the therapeutically effective amount is administered as a single dose or is divided into two, three, or four doses. In some embodiments, ibudilast is administered continually.

In some embodiments, the subject is diagnosed with or suffering from severe viral-induced pneumonia. In some embodiments, the severe viral-induced pneumonia is associated with an infection by an influenza virus, a respiratory syncytial virus, a coronavirus, a rhinovirus, an adenovirus, or a parainfluenza virus. In some embodiments, the infection by a coronavirus is COVID-19.

In some embodiments, the subject is diagnosed with or suffering from mild to severe acute respiratory distress syndrome (ARDS), wherein the subject has positive end-expiratory pressure (PEEP)≥5 cm $H_2O$; and $PaO_2/FiO_2 < 300$ mm Hg. In some embodiments, the subject is diagnosed with or suffering from moderate to severe acute respiratory distress syndrome (ARDS), wherein the subject has positive end-expiratory pressure (PEEP)≥5 cm $H_2O$; and $PaO_2/FiO_2 < 200$ mm Hg. In some embodiments, the ARDS is associated with an infection by an influenza virus, a respiratory syncytial virus, a coronavirus, a rhinovirus, an adenovirus, or a parainfluenza virus. In some embodiments, the infection by a coronavirus is COVID-19.

In some embodiments, the subject is diagnosed with or suffering from cancer. In some embodiments, the cancer is:

a. a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, or a vascular tumor;

b. a cancer of the respiratory tract selected from cancer of the nasal cavity and middle ear, cancer of accessory sinuses, cancer of larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma or mesothelioma;

c. a cancer of the gastrointestinal system selected from squamous cell carcinoma, adenocarcinoma, leiomyosarcoma, lymphoma, carcinoma, ductal adenocarcinoma, insulinoma, glucagonoma, gastrinoma, carcinoid tumors, vipoma, adenocarcinoma, carcinoid tumors, Karposi's sarcoma, hemangioma, lipoma, neurofibroma, fibroma, tubular adenoma, villous adenoma, hamartoma, or leiomyoma;

d. a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, or lipoma;

e. a cancer of the liver selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor or glucagonoma;

f. a cancer of the bone selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma or giant cell tumors;

g. a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma (pinealoma), oligodendroglioma, schwannoma, retinoblastoma, congenital tumors, spinal cord neurofibroma, meningioma, glioma, or sarcoma;

h. a cancer of the reproductive system selected from endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, penile cancer, prostate cancer, or testicular cancer;

i. cancer of the hematologic system selected from myeloid, acute lymphoblastic leukemia, chronic lymphocytic leukemia, myeloproliferative diseases, multiple myeloma, myelodysplastic syndrome, Hodgkin's disease, or non-Hodgkin's lymphoma;

j. a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, or cancer of the hypopharynx;

k. a cancer of the skin selected from malignant melanoma, cutaneous melanoma, basal cell carcinoma, squamous cell carcinoma, Karposi's sarcoma, moles dysplastic nevi, lipoma, angioma, dermatofibroma or keloidal cancer; or l. a cancer selected from cancer of the adrenal glands, neuroblastoma, cancer of connective and soft tissue, cancer of the retroperitoneum and peritoneum, eye cancer, intraocular melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems or secondary malignant neoplasm of other sites.

In some embodiments, the subject is diagnosed with or suffering from microorganism infection. In some embodiments, the microorganism infection is caused by virus, bacteria, fungus, or any combination of two or more thereof.

In some embodiments, the subject is diagnosed with or suffering from sepsis.

In some embodiments, the subject is diagnosed with or suffering from a neurodegenerative disease or disorder. In some embodiments, the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury. In some embodiments, the neurodegenerative disease or disorder is ALS.

In some embodiments, the subject is diagnosed with or suffering from an autoimmune disorder. In some embodiments, the autoimmune disorder is rheumatoid arthritis, IgA nephropathy, vascular disease associated with kidney disease, systemic lupus erythematosus (SLE), Wegener's granulomatosis, relapsing polychondritis, atopic dermatitis, psoriasis, sarcoidosis, Behçet's disease, Vogt-Koyanagi-Harada's disease, uveitis, or idiopathic pulmonary fibrosis.

In some embodiments, ibudilast, or the pharmaceutically acceptable salt thereof, is the only active agent administered to the patient.

In some embodiments, ibudilast, or the pharmaceutically acceptable salt thereof, is administered to the patient with at least one other active agent. In some embodiments, the at least one other active agent is a chemotherapy. In some embodiments, the chemotherapy is an alkylating agent, a topoisomerase inhibitor, a mitotic inhibitor, an antimetabolite, an antibiotic, a proteasome inhibitor, or a tyrosine kinase inhibitor, or any combination of two or more thereof. In some embodiments, the chemotherapy is tumor-infiltrating lymphocyte (TIL) therapy, engineered T-cell receptor (TCR) therapy, chimeric antigen receptor (CAR) T-cell therapy, or natural killer (NK) cell therapy, or any combination of two or more thereof. In some embodiments, the at least one other active agent is selected from an antibiotic, an anti-IL-6 agent, and a TNF-alpha inhibitor or any combination thereof. In some embodiments, the anti-IL-6 agent is selected from tocilizumab, siltuximab, sarilumab, olokizumab, elsilimomab, clazakizumab, sirukumab, and levilimab. In some embodiments, the TNF-alpha inhibitor is selected from etanercept, infliximab, certolizumab, golimumab, and adalimumab. In some embodiments, the antibiotic is selected from penicillins, cephalosporins, macrolides, fluoroquinolones, sulfonamides, tetracyclines, and aminoglycosides.

In some embodiments, a reduction of the plasma level of macrophage migratory inhibitory factor in the subject is observed within 12 hours after a first dose of ibudilast is administered. In some embodiments, a reduction of the plasma level of macrophage migratory inhibitory factor in the subject is observed within 12 hours after administration of ibudilast for 1, 2, 3, 4, 5, 6, 7, 8, 9, or 10 days.

DETAILED DESCRIPTION

The practice of the present disclosure will employ, unless otherwise indicated, conventional methods of chemistry, biochemistry, and pharmacology, within the skill of the art. Such techniques are explained fully in the literature. See, e.g.; A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

Before describing the present disclosure in detail, it is to be understood that this disclosure is not limited to particular administration modes, patient populations, and the like, as such may vary, as will be apparent from the accompanying description.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present disclosure, the following terminology will be used in accordance with the definitions described below.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention. When an embodiment is defined by one of these terms (e.g., "comprising") it should be understood that this disclosure also includes alternative embodiments, such as "consisting essentially of" and "consisting of" for said embodiment.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutraceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent may include ibudilast or a pharmaceutically acceptable salt thereof.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

The terms "subject," "individual" or "patient" are used interchangeably herein and refer to a vertebrate, preferably a mammal. Mammals include, but are not limited to, mice, rodents, rats, simians, humans, farm animals, dogs, cats, sport animals and pets.

The terms "pharmacologically effective amount" or "therapeutically effective amount" of a composition or agent, as provided herein, refer to a nontoxic but sufficient amount of the composition or agent to provide the desired response, such as a reduction or reversal of progressive neurodegenerative diseases. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about," will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

As used herein, the terms "glioblastoma multiforme" or "glioblastoma" "or malignant glioma" are well-understood terms in the art. In some embodiments, "glioblastoma multiforme" or "glioblastoma" or "malignant glioma" are used interchangeably herein and refer to a brain tumor that arises from astrocytes. In some embodiments, glioblastoma is classical glioblastoma, proneural glioblastoma, mesenchymal glioblastoma or neural glioblastoma. In some embodiments, glioblastoma is classical glioblastoma.

As used herein, the term "treatment" or "treating" means any treatment of a disease or condition or associated disorder, in a patient, including inhibiting the disease or condition, that is, arresting or suppressing the development of clinical symptoms, such as cachexia in cancer; and/or relieving the disease or condition that is causing the regression of clinical symptoms, e.g., increasing overall survival or reducing tumor burden.

In some aspects, the term treating refers to an improvement in clinical outcomes. The term "clinical outcome" refers to any clinical observation or measurement relating to a patient's reaction to a therapy. Non-limiting examples of clinical outcomes include tumor response (TR), overall survival (OS), progression free survival (PFS), disease free survival, time to tumor recurrence (TTR), time to tumor progression (TTP), relative risk (RR), toxicity or side effect. "Overall Survival" (OS) intends a prolongation in life expectancy as compared to naïve or untreated individuals or patients. "Progression free survival" (PFS) or "Time to Tumor Progression" (TTP) indicates the length of time during and after treatment that the cancer does not grow. Progression-free survival includes the amount of time patients have experienced a complete response or a partial response, as well as the amount of time patients have experienced stable disease. "Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer. "Time to Tumor Recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up. "Relative Risk" (RR), in statistics and mathematical epidemiology, refers to the risk of an event (or of developing a disease) relative to exposure. Relative risk is a ratio of the probability of the event occurring in the exposed group versus a non-exposed group.

"Treatment" or "treating" includes arresting the development of or reversing the symptom or symptoms of a disease. Non-limiting example of improvements in clinical outcome include longer survival time, reduction in tumor size, non-growth in tumor size, and/or lack of exacerbation in neurological symptoms. Non-limiting examples of neurological symptoms include double vision, vomiting, loss of appetite, changes in mood and personality, changes in ability to think and learn, seizures, speech difficulty, and cognitive impairment.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

The methods of the disclosure are based upon administration of the molecule, ibudilast. Ibudilast is a small molecule drug (molecular weight of 230.3) having the structure shown below.

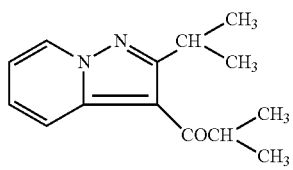

Ibudilast is also found under ChemBank ID 3227, CAS #50847-11-5, and Beilstein Handbook Reference No. 5-24-03-00396. Its molecular formula corresponds to C14H18N2O. Ibudilast is also known by various chemical names including 2-methyl-1-(2-(1-methylethyl)pyrazolo(1,5-a)pyridin-3-yl)1-propanone; 3-isobutyryl-2-isopropylpyrazolo(1,5-a)pyridine; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is Ketas®. Ibudilast, as referred to herein, is meant to include any and all pharmaceutically acceptable salt forms thereof, prodrug forms (e.g., the corresponding ketal), solvates, and the like, as appropriate for use in its intended formulation for administration.

Ibudilast is also a selective inhibitor of cyclic nucleotide phosphodiesterases (PDEs) 3A, 4, 10A1 and 11A1 (Gibson et al., Eur J Pharmacol 538: 39-42, 2006), has toll-like receptor-4 (TLR4) antagonistic activity (Yang et al., Cell Death and Disease (2016) 7, e2234; doi:10.1038/cddis.2016.140) and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: $Ca^{2+}$/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting in the suppression of both pro-inflammatory mediator and neuroactive mediator release. Ibudilast may also suppress the production of pro-inflammatory cytokines (IL-1β, TNF-α) and may enhance the production of the anti-inflammatory cytokines (IL-4, IL-10). References related to the foregoing include the following: Obernolte, R., et al. (1993) "The cDNA of a human lymphocyte cyclic-AMP phosphodiesterase (PDE IV) reveals a multigene family" Gene 129: 239-247; Rile, G., et al. (2001) "Potentiation of ibudilast inhibition of platelet aggregation in the presence of endothelial cells" Thromb. Res. 102: 239-246; Souness, J. E., et al. (1994) "Possible role of cyclic AMP phosphodiesterases in the actions of ibudilast on eosinophil thromboxane generation and airways smooth muscle tone" Br. J. Pharmacol. 111: 1081-1088; Suzumura, A., et al. (1999) "Ibudilast suppresses TNF.alpha. production by glial cells functioning mainly as type III phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" Br. J. Pharmacol. 133: 841-848. With regards to the treatment of cancers of the CNS, ibudilast exhibits good CNS penetration. (Sanftner et al Xenobiotica 2009 39: 964-977).

Ibudilast is also an allosteric inhibitor of p-hydoxyphenylpyruvate (HPP) tautomerase activity of macrophage inhibitory factor (MIF) (Cho et al., PNAS-USA, 2010 June 107: 11313-8), thereby inhibiting the catalytic and chemotactic functions of MIF. It was unexpectedly found by the inventors that ibudilast also lowers plasma level of MIF. Such a decrease in MIF plasma level is unexpected since there is no known connection between allosteric inhibition of MIF and MIF concentration in plasma. However, since MIF is involved in intracellular signaling through activation of CD74 in a complex with CD44 or the chemokine receptors CXCR2 and CXCR4, both the MIF inhibition and decrease in MIF plasma level by ibudilast can minimize the proinflammatory action of MIF.

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Methods of Administration

As set forth above, in one aspect, the present disclosure is directed to a methods of reducing plasma level of macrophage migratory inhibitory factor in a subject in need thereof, the method comprising, consisting essentially of, or consisting of administering to the subject a therapeutically effective amount of ibudilast, or a pharmaceutical salt thereof. Such administration is effective to attenuate or reverse inflammation in the subject. The inflammation is associated with severe pneumonia, ARDS, cancer, microorganism infection, sepsis, or neurodegenerative disease or disorder, with which the subject is diagnosed or from which the subject is suffering. In some embodiments, ibudilast or a pharmaceutically acceptable salt thereof is administered at a daily dosage amount ranging from about 0.1 mg to 720 mg daily, from about 30 mg to 200 mg daily, from about 40 mg to 600 mg daily, or from about 100 mg to 480 mg daily. In some embodiments, a reduction of the plasma level of macrophage migratory inhibitory factor in the subject is observed within 12 hours after a first dose of ibudilast is administered. In some embodiments, a reduction of the plasma level of macrophage migratory inhibitory factor in the subject is observed within 12 hours after administration of ibudilast for 1, 2, 3, 4, 5, 6, 7, 8, 9, or 10 days.

In some embodiments, the subject is diagnosed with or suffering from severe viral-induced pneumonia. Pneumonia may be classified as severe when the heart, the kidneys, or the circulatory system are at risk of failing, or if the lungs can no longer take in enough oxygen. Treatment with an antibiotic infusion in intensive care is then usually needed, sometimes with artificial respiration or additional drugs such as corticosteroids. Severe pneumonia may be defined as including (i) the presence of at least two minor criteria selected from respiratory rate ≥30 breaths per min, ratio of arterial oxygen tension to inspired oxygen fraction <250, bilateral or multilobar pneumonia, systolic blood pressure ≤90 mm Hg, and diastolic blood pressure ≤60 mm Hg; or (ii) the presence of one major criterion selected from the need for mechanical ventilation, septic shock or the need for vasopressors for >4 h, an increase in the size of infiltrates by >50% within 48 h, and acute renal failure. In some embodiments, the severe viral-induced pneumonia is associated with a coronavirus infection. In some embodiments, the coronavirus infection is COVID-19.

In some embodiments, the subject is diagnosed with or suffering from acute respiratory distress syndrome (ARDS). Mild ARDS is characterized by $PaO_2/FiO_2$ of 200 mm Hg to 300 mm Hg. Moderate ARDS is characterized by $PaO_2/FiO_2$ of 100 mm Hg to 200 mm Hg. Severe ARDS is characterized by $PaO_2/FiO_2$<100 mm Hg.

In some embodiments, the subject is diagnosed with or suffering from mild to severe acute respiratory distress syndrome (ARDS), wherein the subject has positive end-expiratory pressure (PEEP)≥5 cm $H_2O$; and $PaO_2/FiO_2$<300 mm Hg. In some embodiments, the mild to severe ARDS is associated with a coronavirus infection. In some embodiments, the coronavirus infection is COVID-19.

In some embodiments, the subject is diagnosed with or suffering from moderate to severe acute respiratory distress syndrome (ARDS), wherein the subject has positive end-expiratory pressure (PEEP)≥5 cm $H_2O$; and $PaO_2/FiO_2$<200 mm Hg. In some embodiments, the moderate to severe ARDS is associated with a coronavirus infection. In some embodiments, the coronavirus infection is COVID-19.

In some embodiments, the subject is diagnosed with or suffering from cancer.

In some embodiments, the cancer is:
a. a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, or a vascular tumor;
b. a cancer of the respiratory tract selected from cancer of the nasal cavity and middle ear, cancer of accessory sinuses, cancer of larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma or mesothelioma;
c. a cancer of the gastrointestinal system selected from squamous cell carcinoma, adenocarcinoma, leiomyosarcoma, lymphoma, carcinoma, ductal adenocarcinoma, insulinoma, glucagonoma, gastrinoma, carcinoid tumors, vipoma, adenocarcinoma, carcinoid tumors, Karposi's sarcoma, hemangioma, lipoma, neurofibroma, fibroma, tubular adenoma, villous adenoma, hamartoma, or leiomyoma;
d. a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, or lipoma;
e. a cancer of the liver selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor or glucagonoma;
f. a cancer of the bone selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma or giant cell tumors;
g. a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma (pinealoma), oligodendroglioma, schwannoma, retinoblastoma, congenital tumors, spinal cord neurofibroma, meningioma, glioma, or sarcoma;
h. a cancer of the reproductive system selected from endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, penile cancer, prostate cancer, or testicular cancer;
i. cancer of the hematologic system selected from myeloid, acute lymphoblastic leukemia, chronic lymphocytic leukemia, myeloproliferative diseases, multiple myeloma, myelodysplastic syndrome, Hodgkin's disease, or non-Hodgkin's lymphoma;
j. a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, or cancer of the hypopharynx;
k. a cancer of the skin selected from malignant melanoma, cutaneous melanoma, basal cell carcinoma, squamous cell carcinoma, Karposi's sarcoma, moles dysplastic nevi, lipoma, angioma, dermatofibroma or keloidal cancer; or
l. a cancer selected from cancer of the adrenal glands, neuroblastoma, cancer of connective and soft tissue, cancer of the retroperitoneum and peritoneum, eye cancer, intraocular melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems or secondary malignant neoplasm of other sites.

In some embodiments, the subject is diagnosed with or suffering from microorganism infection. In some embodiments, the microorganism infection is caused by virus, bacteria, fungus, or any combination of two or more thereof. In some embodiments, the microorganism infection is caused by virus. In some embodiments, the microorganism infection is caused by bacteria. In some embodiments, the microorganism infection is caused by fungus.

In some embodiments, the subject is diagnosed with or suffering from sepsis.

In some embodiments, the subject is diagnosed with or suffering from a neurodegenerative disease or disorder. In some embodiments, the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury. In some embodiments, the neurodegenerative disease or disorder is ALS.

Ibudilast administration may be accomplished through various modes of delivery of ibudilast comprising formulations. Preferred methods of delivery of ibudilast-based therapeutic formulations include systemic and localized delivery. Such routes of administration include but are not limited to, oral, intra-arterial, intrathecal, intraspinal, intramuscular, intraperitoneal, intranasal, and inhalation routes.

More particularly, an ibudilast-based formulation of the present disclosure may be administered for therapy by any suitable route, including without limitation, oral, rectal, nasal, topical (including transdermal, aerosol, buccal and sublingual), vaginal, parenteral (including subcutaneous, intravenous, intramuscular, and intradermal), intrathecal, and pulmonary. In some embodiments, the ibudilast-based formulation is administered orally. In some embodiments, the ibudilast-based formulation is administered through an injection. The preferred route will, of course, vary with the condition and age of the recipient, the particular syndrome being treated, and the specific combination of drugs employed.

In some embodiments, the ibudilast or pharmaceutically acceptable salt thereof is administered orally. In some embodiments, the ibudilast or pharmaceutically acceptable salt thereof is administered through an injection.

An ibudilast composition of the present disclosure, when comprising more than one active agent, may be administered as a single combination composition comprising a combination of ibudilast and at least one additional active agent. In terms of patient compliance and ease of administration, such an approach is preferred, since patients are often averse to taking multiple pills or dosage forms, often multiple times daily, over the duration of treatment. Alternatively, the combination of the disclosure is administered as separate dosage forms. In instances in which the drugs comprising the therapeutic composition of the disclosure are administered as separate dosage forms and co-administration is required, ibudilast and each of the additional active agents may be administered simultaneously, sequentially in any order, or separately.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount of ibudilast or pharmaceutically acceptable salt thereof will range from a total daily dosage of about 0.1 mg/day to 720 mg/day, about 40-600 mg/day, or about 100-480 mg/day, or more preferably, in an amount between about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, the therapeutically effective amount of ibudilast or pharmaceutically acceptable salt thereof is from about 30-200 mg/day, administered as either a single dosage or as multiple dosages. In some embodiments, multiple dosages include two, three, or four doses per day.

Preferred dosage amounts include dosages greater than about 20 mg BID or TID. That is to say, a preferred dosage amount is greater than about 30 mg/day, 60 mg/day, 90 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day or more.

In some embodiments, the therapeutically effective amount of ibudilast or pharmaceutically acceptable salt thereof is at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, or at least 720 mg/day. In some embodiments, the therapeutically effective amount of ibudilast or pharmaceutically acceptable salt thereof is at least 60 mg/day. In some embodiments, the therapeutically effective amount of ibudilast or pharmaceutically acceptable salt thereof is at least 100 mg/day.

Depending upon the dosage amount and precise condition to be treated, administration can be one, two, three, or four times daily for a time course of one day to several days, weeks, months, and even years, and may even be for the life of the patient. Illustrative dosing regimens will last a period of at least about a week, from about 1-4 weeks, from 1-3 months, from 1-6 months, from 1-52 weeks, from 1-24 months, or longer. In some embodiments, the ibudilast or the pharmaceutically acceptable salt thereof is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In some embodiments, the ibudilast or the pharmaceutically acceptable salt thereof is administered for three months or less. In some embodiments, the ibudilast or the pharmaceutically acceptable salt thereof is administered for at least three months. In some embodiments, the ibudilast or the pharmaceutically acceptable salt thereof is administered for at least six months.

In some embodiments, the ibudilast or the pharmaceutically acceptable salt thereof is administered for at least one year. In some embodiments, the ibudilast or the pharmaceutically acceptable salt thereof is administered for at least two years. In some embodiments, the ibudilast or the pharmaceutically acceptable salt thereof is administered for at least three years.

In some embodiments, the therapeutically effective amount of ibudilast or the pharmaceutically acceptable salt thereof is administered in a single dosage per day. In some embodiments, the therapeutically effective amount of ibudilast or the pharmaceutically acceptable salt thereof is administered in two dosages per day. In some embodiments, the therapeutically effective amount of ibudilast or the pharmaceutically acceptable salt thereof is administered in three dosages per day. In some embodiments, the therapeutically effective amount of ibudilast or the pharmaceutically acceptable salt thereof is administered in four dosages per day. In some embodiments, the therapeutically effective amount of ibudilast or the pharmaceutically acceptable salt thereof is administered continually.

In some embodiments, the ibudilast or pharmaceutically acceptable salt thereof is administered at least once daily. In some embodiments, the ibudilast or pharmaceutically acceptable salt thereof is administered at least twice daily. In some embodiments, the ibudilast or pharmaceutically acceptable salt thereof is administered once daily. In some embodiments, the ibudilast or pharmaceutically acceptable salt thereof is administered twice daily.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Formulations

Ibudilast may be administered in a composition of formulation which may optionally contain one or more additional components as described below.

Excipients/Carriers

In addition to ibudilast or a pharmaceutically acceptable salt thereof, the compositions of the disclosure may further comprise one or more pharmaceutically acceptable excipients or carriers. Exemplary excipients include, without limitation, polyethylene glycol (PEG), PEG 400, (2-Hydroxypropyl)β-cyclodextrin, hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the disclosure may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15% to about 95% by weight of the excipient. In general, the amount of excipient present in an ibudilast composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", 19th ed., Williams & Williams, (1995), the "Physician's Desk Reference", 52.sup.nd ed., Medical Economics, Montvale, N.J. (1998), and Kibbe, A. H., Handbook of Pharmaceutical Excipients, 3.sup.rd Edition, American Pharmaceutical Association, Washington, D.C., 2000.

Other Actives

A formulation (or kit) in accordance with the disclosure may contain, in addition to ibudilast or a pharmaceutically acceptable salt thereof, one or more other therapeutic active agents. In some embodiments, the one or more other therapeutic agents comprise a chemotherapy. In some embodiments, the chemotherapy is an alkylating agent (such as, but not limited to, cyclophosphamide, ifosfamide, busulfan, chlorambucil, melphalan, temozolomide, cisplatin, carboplatin, or oxalipatin), a topoisomerase inhibitor (such as, but not limited to, irinotecan, topotecan, etoposide, teniposide, anthracyclines, doxorubicin, daunorubicin, or idarubicin), a mitotic inhibitor (such as, but not limited to, vincristine, vinblastine, docetaxel, or paclitaxel), an antimetabolite (such as, but not limited to, methotrexate, pemetrexed, cytarabine, 5-fluorouracil, gemcitabine, capacitabine, 6-mercaptopurine, azathioprine, cladribine, or hydroxycarbamide), an antibiotic (such as, but not limited to, bleomycin, actinomycin D, or mitomycin), a proteasome inhibitor (such as, but not limited to, bortezomib), or a tyrosine kinase inhibitor (such as, but not limited to, imatinib or erlotinib), or any combination of two or more thereof. In some embodiments, the chemotherapy is tumor-infiltrating lymphocyte (TIL) therapy, engineered T-cell receptor (TCR) therapy, chimeric antigen receptor (CAR) T-cell therapy, or natural killer (NK) cell therapy. In some embodiments, the one or more other therapeutic agents comprise a phosphodiesterase-3 inhibitor. In some embodiments, the one or more other therapeutic agents comprise a phosphodiesterase-4 inhibitor. In some embodiments, the one or more other therapeutic agents comprise a macrophage inhibitory factor inhibitor. In some embodiments, the one or more other therapeutic agents comprise an antibiotic, an anti-IL-6 agent, a TNF-alpha inhibitor, or any combination thereof. In some embodiments, the anti-IL-6 agent is selected from tocilizumab, siltuximab, sarilumab, olokizumab, elsilimomab, clazakizumab, sirukumab, and levilimab. In some embodiments, the TNF-alpha inhibitor is selected from etanercept, infliximab, certolizumab, golimumab, and adalimumab. In some embodiments, the antibiotic is selected from penicillins, such as penicillin or amoxicillin; cephalosporins, such as cephalexin; macrolides, such as erythromycin, clarithromycin, and azithromycin; fluoroquinolones, such as ciprofloxacin, levofloxacin, and ofloxacin; sulfonamides, such as co-trimoxazole and trimethoprim; tetracyclines, such as tetracycline and doxycycline; and aminoglycosides, such as gentamicin and tobramycin. In some embodiments, the antibiotic is vancomycin, cefepime, tobramycin, aztreonam, piperacillin, tazobactam, metronidazole, gentamicin, ceftriaxone, ertapenem, oxacillin, nafcillin, clindamycin, azithromycin, levofloxacin, or any combination of two or more thereof.

Preferably, the one or more other therapeutic agent is one that possesses a mechanism of action different from that of ibudilast. Such active ingredients can be found listed in the FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

The dosage amounts provided above are meant to be merely guidelines; the precise amount of a secondary active agent to be administered during combination therapy with ibudilast or the pharmaceutically acceptable salt thereof will, of course, be adjusted accordingly and will depend upon factors such as intended patient population, the particular progressive neuropathic disease symptom or condition to be treated, potential synergies between the active agents administered, and the like, and will readily be determined by one skilled in the art based upon the guidance provided herein.

Sustained Delivery Formulations

Preferably, the compositions are formulated in order to improve stability and extend the half-life of ibudilast or the pharmaceutically acceptable salt thereof. For example, ibudilast or the pharmaceutically acceptable salt thereof may be delivered in a controlled or extended-release formulation. Controlled or extended-release formulations are prepared by incorporating ibudilast or the pharmaceutically acceptable salt thereof into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast or the pharmaceutically acceptable salt thereof can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; and McGee et al., J. Microencap. (1996).

Extended release polymers suitable for this purpose are known in the art and include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleic anhydride copolymers and the like; ethylacrylate-methylmethacrylate copolymers; aminoalkyl methacrylate copolymers; and mixtures thereof.

Delivery Forms

The ibudilast or pharmaceutically acceptable salt thereof compositions described herein encompass all types of formulations, and in particular, those that are suited for systemic or intrathecal administration. Oral dosage forms include tablets, lozenges, capsules, syrups, oral suspensions, emulsions, granules, and pellets. In some embodiments, the oral dosage form is a tablet. In some embodiments, the tablet is an extended release tablet. In some embodiments, the oral dosage form is a capsule. In some embodiments, the capsule is an extended release capsule.

Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, an ibudilast or pharmaceutically acceptable salt thereof composition of the disclosure is one suited for oral administration.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx® (Aradigm), the Ultravent® (Mallinkrodt), and the Acorn II® (Marquest Medical Products). A composition of the disclosure may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the disclosure are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the disclosure may also be an extended release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the disclosure may optionally include other agents conventional in the pharmaceutical arts and particular type of formulation being employed, for example, for oral administration forms, the composition for oral administration may also include additional agents as sweeteners, thickeners or flavoring agents.

Kits

Also provided herein is a kit containing at least one combination composition of the disclosure, accompanied by instructions for use.

For example, in instances in which each of the drugs themselves are administered as individual or separate dosage forms, the kit comprises ibudilast in addition to each of the drugs making up the composition of the disclosure, along with instructions for use. The drug components may be packaged in any manner suitable for administration, so long as the packaging, when considered along with the instructions for administration, clearly indicates the manner in which each of the drug components is to be administered.

For example, for an illustrative kit comprising ibudilast and one other active agent, the kit may be organized by any appropriate time period, such as by day. As an example, for Day 1, a representative kit may comprise unit dosages of each of ibudilast and the one other active agent. If each of the drugs is to be administered twice daily, then the kit may contain, corresponding to Day 1, two rows of unit dosage forms of each of ibudilast and the one other active agent, along with instructions for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister packs, desiccants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1: A Phase 2, Open-Label Study to Evaluate the Safety, Tolerability and Clinical Response of Ibudilast for the Treatment of Moderate to Severe Pneumonia/ARDS in COVID-19 Patients The study consists of a Screening Phase followed by a Treatment and Follow-up (End of Study) Phase. Following the Screening Phase, if subjects meet entry criteria, subject is administered treatment with ibudilast. Upon completion of the 10-day treatment phase, subject is telephoned for collection of adverse events and concomitant medications.

After initial screening (Screening Phase: up to 3 days), subjects receive ibudilast 100 mg/d (50 mg b.i.d) every day for 10 consecutive days (Treatment Phase). The following screening assessments are performed upon signing the ICF: inclusion/exclusion criteria review, assess clinical status, draw blood for plasma cytokines levels, CRP (C-reactive protein) and PK/biomarker.

On Day 1 (Baseline) of the Treatment Phase, subjects are treated with ibudilast. During the Treatment Phase, the subject will have study-related assessments conducted to collect information on adverse events and concomitant medications.

The patient receives an end of treatment telephone call or visit to assess adverse event status (End of Study Phase).

Primary Outcome: Clinical Status Using 7-Category Ordinal Scale:
1. not hospitalized with resumption of normal activities;
2. not hospitalized but unable to resume normal activities;
3. hospitalized but not requiring supplemental oxygen;
4. hospitalized and requiring supplemental oxygen;
5. hospitalized and requiring nasal high-flow oxygen therapy, noninvasive mechanical ventilation, or both;
6. hospitalized and requiring extracorporeal membrane oxygenation, invasive mechanical ventilation, or both;
7. death.

Secondary Outcomes:
Time to clinical improvement
$PaO_2/FiO_2$ ratio
Plasma cytokines levels (MIF, IL-1 beta, IL-6, etc.)
CRP (C-reactive protein) level
Incidence of mechanical ventilation
Duration of ICU stay
Ventilator free days
Mortality rate
Time to Discharge/Duration of mechanical ventilation
Incidence of Adverse Events Study Entry Criteria:
Inclusion Criteria
1. Written or verbal informed consent by subject or subject representative is obtained
2. Male or female subjects age 18 to 80 years, inclusive
3. COVID-19 pneumonia confirmed with WHO criteria (including a positive PCR of any specimen, e.g., blood, respiratory, stool, urine, or any other body fluid)
4. Confirmed moderate to severe ARDS by Berlin Definition a) Positive end-expiratory pressure (PEEP)≥5 cm $H_2O$ and b) $PaO_2/FiO_2$<200 mm Hg
5. Not intubated
6. Able to swallow capsule (size 4)
7. No known allergies to the study drug or its excipients Exclusion Criteria
1. Suspected active bacterial, fungal, viral or other infection other than COVID-19
2. Known or suspected immunosuppression with immunosuppressant mediations or chemotherapeutic agents
3. Active primary lung cancer or another malignancy metastatic to the lungs
4. Moderate to severe liver failure
a. ALT, AST, Total Bilirubin >3×ULN
5. Severe COPD (stage III or severe according to the GOLD Classification)
6. On home ventilator support or continuous domiciliary $O_2$ therapy for baseline lung disease
7. Active tuberculosis (TB) infection
8. Life expectancy less than 24 hours
9. Patients already intubated and on ventilator support
10. Female subjects must not be lactating or pregnant at Screening or Baseline;
11. History of stomach or intestinal surgery or any other condition that could interfere with or is judged by the Investigator to interfere with absorption, distribution, metabolism, or excretion of study drug
12. Treatment with an investigational drug within 5 half-lives or 30 days whichever is longer prior to study drug treatment
13. Any other serious medical condition or abnormality that, in the Investigator's opinion, would preclude participation in the study Schedule of Assessments
Informed Consent: during Screening Phase
Inclusion/exclusion criteria review: during Screening Phase and Day 1 of Treatment Phase
Assess Clinical Status: during Screening Phase; Days 1-10 of Treatment Phase; and Follow-up Telephone Call/Visit
C-reactive protein: during Screening Phase; Days 1, 3, 7, and 10 of Treatment Phase
PK blood sample: during Screening Phase; Days 1, 3, 5, 7, and 10 of Treatment Phase
Biomarker blood samples (MIF, IL-1b): Days 1-10 of Treatment Phase
Administer Study Drug: Days 1-10 of Treatment Phase
Adverse event review: Days 1-10 of Treatment Phase; and Follow-up Telephone Call/Visit
Concomitant medications review: Days 1-10 of Treatment Phase The respiratory status of the subjects is expected to improve by end of Treatment Phase with respect to initial assessment during the Screening Phase. Treatment with ibudilast is expected to lower MIF plasma level of the subjects by end of Treatment Phase compared to MIF plasma level as measured during the Screening Phase. Plasma levels of IL-1 beta, IL-6, and CRP are expected to decrease by end of Treatment Phase compared to their respective levels as measured during the Screening Phase.

Example 2: A Multi-Center, Open-Label Biomarker Study to Evaluate Ibudilast in Subjects with Amyotrophic Lateral Sclerosis (ALS)

This was a multi-center, open-label study with a 6 weeks Screening Phase, 36 weeks Treatment Phase, and a Follow-up Phase 4 weeks after the last dose. Ibudilast was orally administered 50 mg b.i.d. for a total daily dose of 100 mg/day.

The objectives of the Study were (i) to measure the impact of ibudilast on [11C]-PBR28 uptake in the motor cortices and brain stem measured by positron emission tomography (PET) imaging at 24 weeks; (ii) to measure the impact of ibudilast on several markers of neuro-inflammation measured by blood biomarkers; and (iii) to evaluate safety and tolerability.

Out of the 46 patients screened, eleven (11) individuals were screen failures. Total of the 35 enrolled subjects were enrolled. Of the 35 enrolled subjects, 16 subjects (45.7%) terminated the study early, and 19 subjects completed the trial. Of these 16 early study withdrawals, 11 (68.8%) were attributed to AEs and 5 (31.2%) were attributed to consent withdrawn.

Serum samples for the 19 subjects who completed the study were evaluated for MIF level before treatment and after treatment with ibudilast.
Mean (SD) pre-treatment serum MIF=422,989 (233,440) pg/ml
Mean (SD) post-treatment serum MIF=300,922 (113,843) pg/ml
Mean (SE) change/month=−19, 845 (8934) pg/ml (p=0.03)

Example 3: A Randomized, Double-Blind, Placebo-Controlled Parallel Group Study to Evaluate the Efficacy, Safety, Tolerability, Biomarkers, and PK of Ibudilast in COVID-19 Subjects at Risk for Developing Acute Respiratory Distress Syndrome (ARDS)

The study consisted of a Screening Phase followed by a Treatment and Follow-up Phase. Following the Screening Phase, if the subject met eligibility criteria, subject was administered treatment with ibudilast or placebo. Subjects received ibudilast 100 mg/d (50 mg b.i.d) or placebo every day for 7 days. Upon completion of the 7-day Treatment Phase, subject was followed-up at Day 14 and at Day 28 post baseline.

The primary objectives are to evaluate the:
efficacy of ibudilast vs. placebo in COVID-19 subjects measured by the proportion of subjects free of respiratory failure (i.e., decreased need for $O_2$ therapy) at Day 7;
efficacy of ibudilast vs. placebo in COVID-19 subjects measured by clinical status (i.e., improvement on NIAID scale) at Day 7; and
anti-inflammatory effects of ibudilast vs. placebo on cytokine levels in COVID-19 subjects.

The secondary objectives are to evaluate the:
safety and tolerability of ibudilast vs. placebo in COVID-19 subjects;
efficacy of ibudilast vs. placebo in COVID-19 subjects measured by the proportion of subjects free of respiratory failure (i.e., decreased need for $O_2$ therapy) at Day 14;
efficacy of ibudilast vs. placebo in COVID-19 subjects measured by clinical status (i.e., improvement on NIAID scale) at Day 14; and
pharmacokinetics of ibudilast vs. placebo in COVID-19 subjects.

Screening Phase (Up to 3 Days).
The following screening assessments were performed upon signing the ICF: inclusion/exclusion criteria review, physical examination, assess vital signs and $O_2$ use, clinical status using the NIAID scale, ECG, draw blood for plasma cytokines that include: migration inhibitory factor (MIF), interleukin 1-beta (IL-1β), interleukin 6 (IL-6), tumor necrosis factor (TNF-α), and C-reactive protein (CRP). Pharmacokinetic (PK) samples, complete blood count (CBC), comprehensive metabolic panel (CMP), D-dimer, and coagulation tests were also be drawn. A serum pregnancy test was done in non-menopausal females. The use of prior medication taken was recorded for 7 days prior to Day 1.

Treatment Phase (7 Days).

On Day 1 (Baseline) of the Treatment Phase, hospitalized subjects were treated with ibudilast (oral, 50 mg (5 capsules) b.i.d) or placebo for a 7-day period. Subjects underwent study-related procedures including physical examination, vital signs, clinical status assessment using the NIAID scale, $O_2$ use, ECG, blood collection of biomarkers, PK, CBC, CMP, D-dimer and coagulation and information on adverse events and concomitant medications were recorded.

Follow-Up Phase.

The Follow-up Phase consisted of two visits, Day 14 (±3 d) and Day 28 (±3 d).

Day 14 (in-patient): On Day 14, conducted physical examination, clinical status, vital signs and $O_2$ use, ECG, CBC, CMP, D-dimer, and coagulation tests, biomarkers, AE and conmed review, and recorded survival status.

Day 28 (telephone follow-up if patient was no longer hospitalized) On Day 28, clinical status and survival status were recorded.

Study Entry Criteria:

Inclusion Criteria

1. Written or verbal informed consent by subject or subject representative is obtained
2. Male or female subjects age 18 to 80 years, inclusive
3. SARS-CoV-2 infection confirmed with WHO criteria (including a positive PCR of any specimen, (e.g., blood, respiratory, stool, urine, or any other body fluid)
4. Chest imaging (radiograph, CT scan or lung ultrasound) with abnormalities consistent with COVID-19 pneumonia
5. $SpO_2 \leq 92\%$ on room air (RA), $RR \geq 24$ breaths per min on RA, and/or requirement for supplemental oxygen
6. At least 1 risk factor which may put patient at higher risk for more severe illness from COVID-19: Age >65, underlying serious heart disease, chronic lung disease, moderate to severe asthma, body mass index of ≥40 or diabetes
7. C-reactive protein >35 mg/L
8. No known allergies to the study drug or its excipients Exclusion Criteria 1. Suspected active bacterial, fungal, viral or other cause of respiratory failure other than COVID-19
2. Subject is already intubated and on ventilator support
3. Known or suspected immunosuppression with immunosuppressant medications or chemotherapeutic agents
4. Active primary lung cancer or another metastatic malignancy to the lungs
5. Moderate to severe liver failure (see section 12.4) defined by Child-Pugh score of ≥7 measured by:
   Total bilirubin
   Serum albumin
   INR
   Ascites
   Hepatic encephalopathy
6. Abnormal CBC defined by:
   Platelet Count <75,000/mm³
   White Blood Count <2500/mm³
7. Subject is on dialysis
8. On home ventilator support or continuous domiciliary $O_2$ therapy for baseline lung disease
9. Active tuberculosis (TB) infection
10. Lactating or pregnant at Screening
11. History of stomach or intestinal surgery or any other condition that could interfere with or is judged by the Investigator to interfere with absorption, distribution, metabolism, or excretion of study drug
12. Treatment with an investigational drug or off-label medication within 5 half-lives or 30 days whichever is longer prior to study drug treatment
13. Participating in another COVID-19 clinical trial
14. Any other serious medical condition or abnormality that, in the Investigator's opinion, would preclude participation in the study.

Primary Endpoints:

Proportion of subjects free from respiratory failure as defined by the need for decreased oxygen requirements (invasive mechanical ventilation, non-invasive ventilation, high-flow oxygen, or ECMO, CPAP, BiPAP, nasal cannula) at Day 7

Mean change from baseline in clinical status using the NIAID 8-point ordinal scale at Day 7

Percentage of patients with at least a one-point improvement in clinical status using the NIAID 8-point ordinal scale at Day 7

Mean change from baseline in migration inhibitory factor (MIF), interleukin 1-beta (IL-1β), interleukin 6 (IL-6), tumor necrosis factor (TNF-α), and C-reactive protein (CRP) at Day 7

Secondary Endpoints:

Incidence, frequency and severity of adverse events at Day 7 and Day 14

Mean change from baseline of the following parameters at Day 7:
  Mean change from baseline in ALT
  Mean change from baseline in AST
  Mean change from baseline in serum creatinine
  Mean change from baseline in BUN
  Mean change from baseline in complete blood count
  Mean change from baseline total bilirubin
  Mean change from baseline in D-dimer Proportion of subjects free from respiratory failure as defined by the need for decreased oxygen requirement (invasive mechanical ventilation, non-invasive ventilation, high-flow oxygen, or ECMO, CPAP, BiPAP, nasal cannula) at Day 14

Mean change from baseline in clinical status using the NIAID 8-point ordinal scale at Day 14 and Day 28

Incidence of mechanical ventilation/intubation at Day 7 and Day 14

Incidence of ICU admission

PK plasma concentrations

All-cause mortality at Days 7, 14, 28

The clinical status evaluated with NIAID scale, respiratory status (oxygen requirement, SpO2, use of ventilator) of the subjects is expected to improve by end of Treatment Phase with respect to initial assessment during the Screening Phase. Plasma levels of TNF-α, IL-1 beta, IL-6, and CRP are expected to decrease by end of Treatment Phase compared to their respective levels as measured during the Screening Phase.

Treatment with ibudilast was expected to lower MIF plasma level of the subjects by end of Treatment Phase compared to MIF plasma level as measured during the Screening Phase. Plasma levels of MIF in eight patients either treated with ibudilast or placebo are shown below:

Ibudilast-Treated Group Plasma MIF Level (pg/mL)

| Subject | A | B | C | D | Mean | SD |
|---|---|---|---|---|---|---|
| pre-treatment | 25267 | 21130 | 17763 | 27005 | 22791.3 | 3603.1 |
| post-treatment | 14137 | 19633 | 5726 | 8572 | 12017 | 5337.2 |
| difference | −11130 | −1497 | −12037 | −18433 | −10774.3 | 6050.7 |

Placebo Group Plasma MIF Level (pg/mL)

| Subject | E | F | G | H | Mean | SD |
|---|---|---|---|---|---|---|
| pre-treatment | 30777 | 23353 | 7743 | 10755 | 18157 | 9347.5 |
| post-treatment | 31436 | 31901 | 22497 | 12805 | 24659.8 | 7803.3 |
| difference | 659 | 8548 | 14754 | 2050 | 6502.8 | 5617.9 |

| | ibudilast | placebo |
|---|---|---|
| Mean (SD) pre-treatment MIF level pg/ml | 22791.3 (3603.1) | 18157 (9347.5) |
| Mean (SD) post-treatment MIF level pg/ml | 12017 (5337.2) | 24699.8 (7803.3) |
| Mean change MIF level (SD) pg/ml | −110774.3 (6050.7) | 6502.8 (5617.9) |

Difference of mean change of MIF level (pg/ml) between ibudilast-treated group and placebo group=17277 pg/ml (p value=0.00552).

Para. A. A method of reducing plasma level of macrophage migratory inhibitory factor in a subject in need thereof, the method comprising administering to the subject a therapeutically effective amount of ibudilast, or a pharmaceutical salt thereof.

Para. B. The method of Para. A, wherein ibudilast, or the pharmaceutically acceptable salt thereof, is administered orally.

Para. C. The method of Para. A, wherein ibudilast, or the pharmaceutically acceptable salt thereof, is administered intravenously.

Para. D. The method of Para. A, wherein ibudilast, or the pharmaceutically acceptable salt thereof, is administered by subcutaneous injection.

Para. E. The method of Para. A, wherein ibudilast, or the pharmaceutically acceptable salt thereof, is administered by intramuscular injection.

Para. F. The method of Para. A, wherein ibudilast, or the pharmaceutically acceptable salt thereof, is administered by inhalation.

Para. G. The method of any one of Paras. A-F, wherein ibudilast, or the pharmaceutically acceptable salt thereof, is administered for 1, 2, 3, 4, 5, 6, 7, 8, 9, or 10 days, or more.

Para. H. The method of any one of Paras. A-F, wherein ibudilast, or the pharmaceutically acceptable salt thereof, is administered for at least 3 months.

Para. I. The method of any one of Paras. A-F, wherein ibudilast, or the pharmaceutically acceptable salt thereof, is administered for at least one year.

Para. J. The method of any one of Paras. A-F, wherein ibudilast, or the pharmaceutically acceptable salt thereof, is administered for at least two years.

Para. K. The method of any one of Paras. A-J, wherein ibudilast, or the pharmaceutically acceptable salt thereof, is administered at least once daily.

Para. L. The method of any one of Paras. A-J, wherein ibudilast, or the pharmaceutically acceptable salt thereof, is administered twice daily.

Para. M. The method of any one of Paras. A-L, wherein the therapeutically effective amount of ibudilast, or the pharmaceutically acceptable salt thereof, is from 0.1 mg to 720 mg per day.

Para. N. The method of any one of Paras. A-L, wherein the therapeutically effective amount of ibudilast, or the pharmaceutically acceptable salt thereof, is from 30 mg to 200 mg per day.

Para. O. The method of any one of Paras. A-L, wherein the therapeutically effective amount of ibudilast, or the pharmaceutically acceptable salt thereof, is 40 mg to 600 mg daily.

Para. P. The method of any one of Paras. A-L, wherein the therapeutically effective amount of ibudilast, or the pharmaceutically acceptable salt thereof, is 100 mg to 480 mg daily.

Para. Q. The method of any one of Paras. A-L, wherein the therapeutically effective amount of ibudilast, or the pharmaceutically acceptable salt thereof, is selected from the group consisting of 30 mg/day, 60 mg/day, 90 mg/day, 100 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

Para. R. The method of any one of Paras. A-Q, wherein the therapeutically effective amount is administered as a single dose or is divided into two, three, or four doses.

Para. S. The method of any one of Paras. A-Q, wherein ibudilast is administered continually.

Para. T. The method of any one of Paras. A-S, wherein the subject is diagnosed with or suffering from severe viral-induced pneumonia.

Para. U. The method of Para. T, wherein the severe viral-induced pneumonia is associated with an infection by an influenza virus, a respiratory syncytial virus, a coronavirus, a rhinovirus, an adenovirus, or a parainfluenza virus.

Para. V. The method of Para. U, wherein the infection by a coronavirus is COVID-19.

Para. W. The method of any one of Paras. A-S, wherein the subject is diagnosed with or suffering from mild to severe acute respiratory distress syndrome (ARDS), wherein the subject has positive end-expiratory pressure (PEEP)≥5 cm $H_2O$; and $PaO_2/FiO_2$<300 mm Hg.

Para. X. The method of Para. W, wherein the subject is diagnosed with or suffering from moderate to severe acute respiratory distress syndrome (ARDS), wherein the subject has positive end-expiratory pressure (PEEP)≥5 cm $H_2O$; and $PaO_2/FiO_2$<200 mm Hg.

Para. Y. The method of Para. W or Para. X, wherein the ARDS is associated with an infection by an influenza virus, a respiratory syncytial virus, a coronavirus, a rhinovirus, an adenovirus, or a parainfluenza virus.

Para. Z. The method of Para. Y, wherein the infection by a coronavirus is COVID-19.

Para. AA. The method of any one of Paras. A-S, wherein the subject is diagnosed with or suffering from cancer.

Para. AB. The method of Para. AA, wherein the cancer is:
a. a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, or a vascular tumor;
b. a cancer of the respiratory tract selected from cancer of the nasal cavity and middle ear, cancer of accessory sinuses, cancer of larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma or mesothelioma;

c. a cancer of the gastrointestinal system selected from squamous cell carcinoma, adenocarcinoma, leiomyosarcoma, lymphoma, carcinoma, ductal adenocarcinoma, insulinoma, glucagonoma, gastrinoma, carcinoid tumors, vipoma, adenocarcinoma, carcinoid tumors, Karposi's sarcoma, hemangioma, lipoma, neurofibroma, fibroma, tubular adenoma, villous adenoma, hamartoma, or leiomyoma;

d. a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, or lipoma;

e. a cancer of the liver selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor or glucagonoma;

f. a cancer of the bone selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma or giant cell tumors;

g. a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma (pinealoma), oligodendroglioma, schwannoma, retinoblastoma, congenital tumors, spinal cord neurofibroma, meningioma, glioma, or sarcoma;

h. a cancer of the reproductive system selected from endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, penile cancer, prostate cancer, or testicular cancer;

i. cancer of the hematologic system selected from myeloid, acute lymphoblastic leukemia, chronic lymphocytic leukemia, myeloproliferative diseases, multiple myeloma, myelodysplastic syndrome, Hodgkin's disease, or non-Hodgkin's lymphoma;

j. a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, or cancer of the hypopharynx;

k. a cancer of the skin selected from malignant melanoma, cutaneous melanoma, basal cell carcinoma, squamous cell carcinoma, Karposi's sarcoma, moles dysplastic nevi, lipoma, angioma, dermatofibroma or keloidal cancer; or l. a cancer selected from cancer of the adrenal glands, neuroblastoma, cancer of connective and soft tissue, cancer of the retroperitoneum and peritoneum, eye cancer, intraocular melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems or secondary malignant neoplasm of other sites.

Para. AC. The method of any one of Paras. A-S, wherein the subject is diagnosed with or suffering from microorganism infection.

Para. AD. The method of Para. AC, wherein the microorganism infection is caused by virus, bacteria, fungus, or any combination of two or more thereof.

Para. AE. The method of any one of Paras. A-S, wherein the subject is diagnosed with or suffering from sepsis.

Para. AF. The method of any one of Paras. A-S, wherein the subject is diagnosed with or suffering from a neurodegenerative disease or disorder.

Para. AG. The method of Para. AF, wherein the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

Para. AH. The method of Para. AG, wherein the neurodegenerative disease or disorder is ALS.

Para. AI. The method of any one of Paras. A-S, wherein the subject is diagnosed with or suffering from an autoimmune disorder.

Para. AJ. The method of Para. AI, wherein the autoimmune disorder is rheumatoid arthritis, IgA nephropathy, vascular disease associated with kidney disease, systemic lupus erythematosus (SLE), Wegener's granulomatosis, relapsing polychondritis, atopic dermatitis, psoriasis, sarcoidosis, Behçet's disease, Vogt-Koyanagi-Harada's disease, uveitis, or idiopathic pulmonary fibrosis.

Para. AK. The method of any one of Paras. A-AJ, wherein ibudilast, or the pharmaceutically acceptable salt thereof, is the only active agent administered to the patient.

Para. AL. The method of any one of Paras. A-AJ, wherein ibudilast, or the pharmaceutically acceptable salt thereof, is administered to the patient with at least one other active agent.

Para. AM. The method of Para. AL, wherein the at least one other active agent is a chemotherapy.

Para. AN. The method of Para. AM, wherein the chemotherapy is an alkylating agent, a topoisomerase inhibitor, a mitotic inhibitor, an antimetabolite, an antibiotic, a proteasome inhibitor, or a tyrosine kinase inhibitor, or any combination of two or more thereof.

Para. AO. The method of Para. AM, wherein the chemotherapy is tumor-infiltrating lymphocyte (TIL) therapy, engineered T-cell receptor (TCR) therapy, chimeric antigen receptor (CAR) T-cell therapy, or natural killer (NK) cell therapy, or any combination of two or more thereof.

Para. AP. The method of Para. AL, wherein the at least one other active agent is selected from an antibiotic, an anti-IL-6 agent, and a TNF-alpha inhibitor or any combination thereof.

Para. AQ. The method of Para. AP, wherein the anti-IL-6 agent is selected from tocilizumab, siltuximab, sarilumab, olokizumab, elsilimomab, clazakizumab, sirukumab, and levilimab.

Para. AR. The method of Para. AP, wherein the TNF-alpha inhibitor is selected from etanercept, infliximab, certolizumab, golimumab, and adalimumab.

Para. AS. The method of Para. AN or Para. AP, wherein the antibiotic is selected from penicillins, cephalosporins, macrolides, fluoroquinolones, sulfonamides, tetracyclines, and aminoglycosides.

Para. AT. The method of any one of Paras. A-AS, wherein a reduction of the plasma level of macrophage migratory inhibitory factor in the subject is observed within 12 hours after a first dose of ibudilast is administered.

Para. AU. The method of any one of Paras. A-AS, wherein a reduction of the plasma level of macrophage migratory inhibitory factor in the subject is observed within 12 hours after administration of ibudilast for 1, 2, 3, 4, 5, 6, 7, 8, 9, or 10 days.

EQUIVALENTS

It should be understood that although the present disclosure has been specifically disclosed by certain embodiments and optional features, modification, improvement and variation of the disclosures embodied disclosed herein may be resorted to by those skilled in the art, and that such modifications, improvements and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

What is claimed is:

1. A method of reducing plasma level of macrophage migratory inhibitory factor in a subject in need thereof, the method comprising administering to the subject a therapeutically effective amount of ibudilast, or a pharmaceutically acceptable salt thereof, wherein the subject is diagnosed with or suffering from severe viral-induced pneumonia.

2. The method of claim 1, wherein ibudilast, or the pharmaceutically acceptable salt thereof, is administered orally.

3. The method of claim 1, wherein ibudilast, or the pharmaceutically acceptable salt thereof, is administered intravenously.

4. The method of claim 1, wherein ibudilast, or the pharmaceutically acceptable salt thereof, is administered for at least 1 day.

5. The method of claim 1, wherein the therapeutically effective amount of ibudilast, or the pharmaceutically acceptable salt thereof, is from 0.1 mg to 720 mg per day.

6. The method of claim 1, wherein the therapeutically effective amount is administered as a single dose or is divided into two, three, or four doses.

7. The method of claim 1, wherein the severe viral-induced pneumonia is associated with an infection by an influenza virus, a respiratory syncytial virus, a coronavirus, a rhinovirus, an adenovirus, or a parainfluenza virus.

8. The method of claim 7, wherein the infection by a coronavirus is COVID-19.

9. The method of claim 1, wherein a reduction of the plasma level of macrophage migratory inhibitory factor in the subject is observed within 12 hours after a first dose of ibudilast is administered.

10. The method of claim 1, wherein a reduction of the plasma level of macrophage migratory inhibitory factor in the subject is observed within 12 hours after administration of ibudilast for 1, 2, 3, 4, 5, 6, 7, 8, 9, or 10 days.

11. The method of claim 1, wherein the therapeutically effective amount of ibudilast, or the pharmaceutically acceptable salt thereof, is about 100 mg per day.

* * * * *

UNITED STATES PATENT AND TRADEMARK OFFICE
CERTIFICATE OF CORRECTION

| | | |
|---|---|---|
| PATENT NO. | : 12,213,966 B2 | Page 1 of 1 |
| APPLICATION NO. | : 17/222673 | |
| DATED | : February 4, 2025 | |
| INVENTOR(S) | : Iwaki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 223 days.

Signed and Sealed this
Second Day of September, 2025

Coke Morgan Stewart
*Acting Director of the United States Patent and Trademark Office*